United States Patent [19]
Carideo, Jr.

[11] Patent Number: 5,201,773
[45] Date of Patent: Apr. 13, 1993

[54] ARTICULATING SUPRACONDYLAR SUSPENSION

[76] Inventor: Joseph F. Carideo, Jr., 1560 Powder Ridge Ct., Palm Harbor, Fla. 34683

[21] Appl. No.: 872,574

[22] Filed: Apr. 23, 1992

[51] Int. Cl.$^5$ ............................. A61F 2/60; A61F 2/78
[52] U.S. Cl. ........................................ 623/32; 623/33; 623/57
[58] Field of Search ............................ 623/32, 33–36, 623/27, 57, 58

[56] References Cited
U.S. PATENT DOCUMENTS

| | | | |
|---|---|---|---|
| 2,402,327 | 6/1946 | Harrington | 623/32 |
| 2,669,728 | 2/1954 | Ritchie | 623/33 X |
| 3,461,464 | 8/1969 | Lindgren | 623/32 X |

Primary Examiner—Ronald Frinks
Attorney, Agent, or Firm—Joseph C. Mason, Jr.; Ronald E. Smith

[57] ABSTRACT

A device that is pivotally mounted to a socket of a prosthesis has a top part that bears against the residual limb above a bone to suspend the socket from the limb. As the knee is bent, the device pivots about its pivot point and therefore remains in contact with the limb throughout the entire range of motion of the limb so that the socket does not come off. A convexity is formed in the top part of the device, and that convexity bears against the residual limb just above the medial femoral condyle. Another curvature in the top part allows it to at least partially extend around the medial part of the residual limb. The device is substantially rigid but flexible enough to allow it to conform itself to the contour of the residual limb so that the device will fit numerous individuals having differing bone structures. Use of the device eliminates the need to form the convexity into the socket itself.

6 Claims, 2 Drawing Sheets

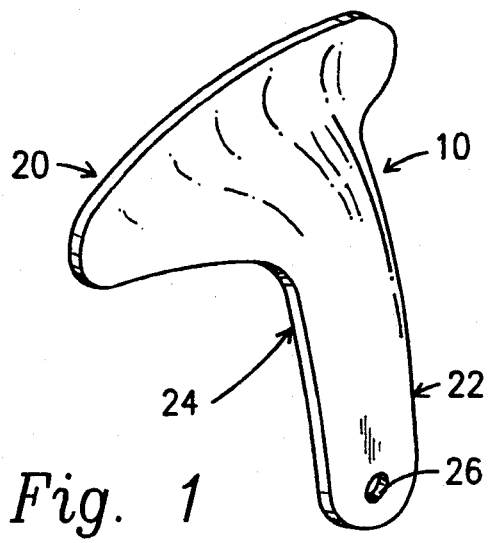
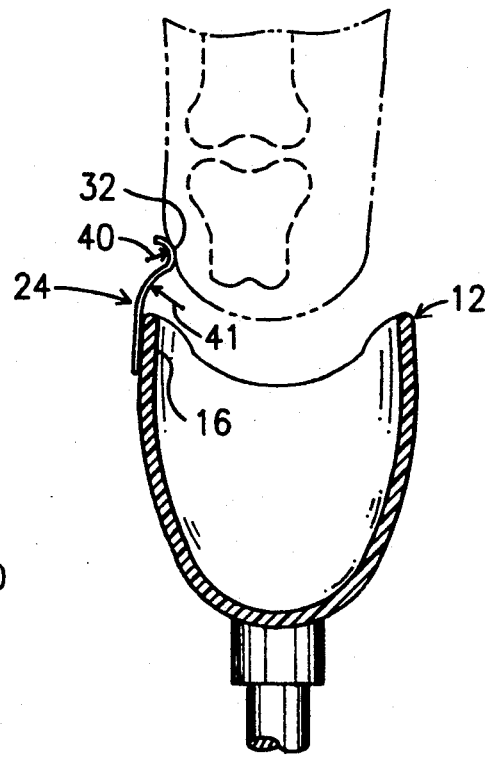
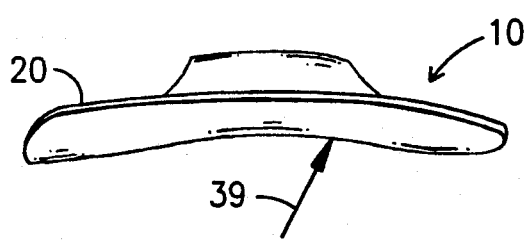
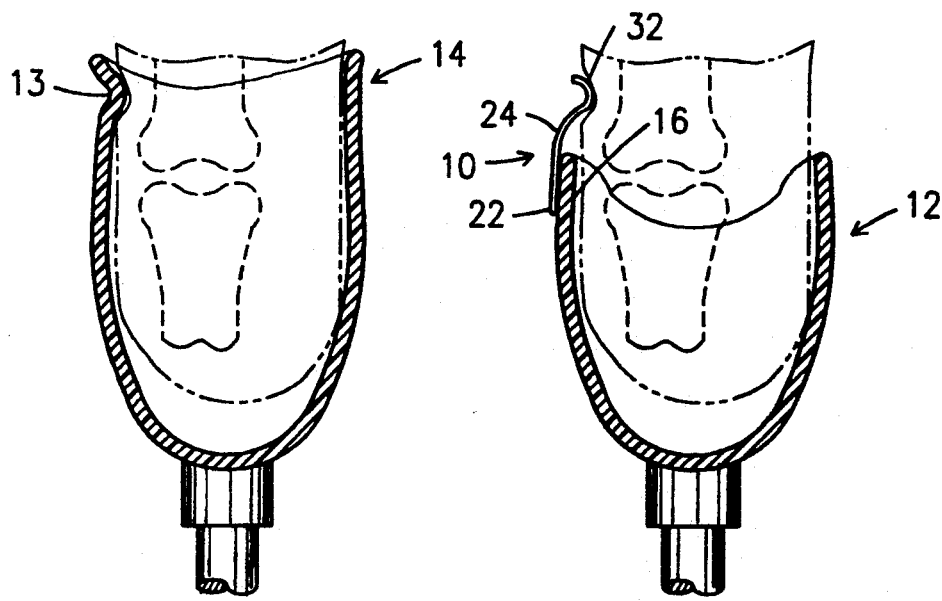
Fig. 1
Fig. 2
Fig. 3
PRIOR ART
Fig. 4
Fig. 5

5,201,773

ARTICULATING SUPRACONDYLAR SUSPENSION

BACKGROUND OF THE INVENTION

1. Field of the Invention

This invention relates to the field of prosthetics. More particularly, it relates to a device that helps retain a socket on the residual limb of a below-the-knee amputee.

2. Description of the Prior Art

A supracondylar patella tendon bearing prosthesis (PTB/SC) is a well known prosthesis used by below-the-knee amputees. It includes an uppermost rim that is specifically contoured to fit over the medial femoral condyle. That bone protrudes to some extent on all non-obese people, and thus is used as a prominence from which the prosthesis may be suspended.

There are a number of problems with this well-known apparatus. Since the uppermost rim must be molded to fit over the medial femoral condyle of the patient, an exacting custom fit must be made for each patient. Moreover, even the best of fits allows the prosthesis to "piston" as the patient walks, i.e., the prosthesis rides up and down on the patient's residual limb. Perhaps even more problematic is the tendency of the prosthesis to come off when the patient's leg is bent beyond the normal bending of walking. For example, climbing a ladder with the conventional PTB/SC prosthesis may cause it to come detached because the medial femoral condyle slides out from under the molded rim of the device; when that happens, the device is no longer suspended from such bone, i.e., the socket detaches from the residual limb.

Thus, the three major problems with the PTB/SC currently in widespread use are the expense and time required to make it, the pistoning effect it exhibits, and its tendency to come off when the knee is bent beyond the design limits of the PTB/SC.

The conventional wisdom has been that all three of these problems can be solved, at least to some extent, by paying more attention to the customized fit of each patient, i.e., by trying to perfect existing techniques. According to this theory, if the perfect fit could be obtained, then the pistoning effect would be lessened and the prosthesis would be less likely to come off. However, even if the perfect fit could be obtained, it would require even more time and expense. Just as importantly, the pistoning effect and the occasional detachment would still occur from time to time.

Other approaches to the problem include establishing a vacuum in the bottom of the PTB in an attempt to reduce reliance upon the medial femoral condyle as a suspension means. That approach requires the addition of a check valve to the socket; that makes the prosthesis even more expensive.

Thus, developments in this art are leading either towards perfection of the fit of the PTB over the medial femoral condyle, or towards vacuuming techniques that eschew use of that bone altogether. Accordingly, it follows that the invention disclosed hereinafter, which relies upon neither vacuuming nor custom fitting, would not have been obvious at the time it was made to those of ordinary skill in this art.

SUMMARY OF THE INVENTION

The present invention vitiates the need to custom fit a PTB/SC prosthesis over the medial femoral condyle of a patient, but does not rely upon a vacuum to maintain the prosthesis on the residual limb. In accordance with the teachings of this invention, the bone-matching curvature molded into the uppermost rim of a conventional PTB/SC prosthesis at painstaking time and expense is no longer needed; such uppermost rim area is actually eliminated by the novel design, and considerable savings of time and expense are thereby realized. The invention may be used, however, in connection with such conventional prostheses; the custom-molded upper rim region is simply cut off and replaced with the novel apparatus.

In lieu of the form-fitting PTB of the prior art, the present invention provides a one-size-fits-all flexible member having a first end that fits over the medial femoral condyle of all persons except the obese and a second end that is pivotally connected to the PTB prosthesis. The articulation provided by the pivotal mounting enables the patient to bend the knee to any extent without risk of prosthesis detachment, because the first end of the device remains in fitting relation to the medial femoral condyle, by means of a strap, at any angle of bending. The precise curvature of the uppermost rim of the prosthesis is eliminated in its entirety by either making the prosthesis as original equipment without the curved uppermost rim or by severing said rim from an existing prosthesis to enable retrofitting of the novel device as aforesaid.

The first end of the device has a first curvature that extends toward the anterior side of the knee and toward the posterior side thereof, i.e., the first curvature wraps around the medial femoral condyle, at least to some extent. A second curvature is formed in the first end as well and extends the entire extent of the first-mentioned curvature. That second curvature is an elongate convexity relative to the patient's knee, or an elongate concavity if considered from its opposite side. The convexity fits over the medial femoral condyle in much the same way as the form-fitting uppermost rim of the PTB prosthesis of the prior art. However, due to the flexibility of the novel device, it need not be custom fit for individual patients.

An elongate, flexible neck interconnects the first end and the second end of the device, and a third curvature is formed in said neck so that the first end of the device is offset from the second end thereof. This enables attachment of the second end to the socket and placement of the first end in abutting relation to the patient's knee, just above the medial femoral condyle.

An aperture is formed in the second end to facilitate its pivotal mounting to the PTB. A mating aperture is formed in the PTB just downwardly of its uppermost rim so that a pivot pin extending through both apertures provides the articulating joint.

The primary object of the present invention is to obviate the need for custom fitting PTB prosthetic devices to below-the-knee amputees.

Another object is to provide an attachment means that reduces the pistoning effect when a patient walks or runs.

Still another object is to provide an attachment means that maintains the prosthesis on the residual limb even when the knee is bent at an acute angle.

Another very important object is to achieve all of the foregoing objects with a mass-producible, inexpensive device that can be easily mounted to a conventional PTB prosthesis.

These and other important objects, features and advantages of the invention will become apparent as this description proceeds.

The invention accordingly comprises the features of construction, combination of elements and arrangement of parts that will be exemplified in the construction hereinafter set forth, and the scope of the invention will be indicated in the claims.

BRIEF DESCRIPTION OF THE DRAWINGS

For a fuller understanding of the nature and objects of the invention, reference should be made to the following detailed description, taken in connection with the accompanying drawings, in which:

FIG. 1 is a perspective view of the novel device;

FIG. 2 is a top plan view thereof;

FIG. 3 is a front sectional view of a prior art PTB prosthesis;

FIG. 4 is a front sectional view of the novel device when attached to a prosthesis;

FIG. 5 is a front sectional view showing the novel device attached to a prosthesis and a residual limb in spaced relation thereto;

Similar reference numerals refer to similar parts throughout the several views of the drawings.

DETAILED DESCRIPTION OF THE PREFERRED EMBODIMENT

Figure 7:
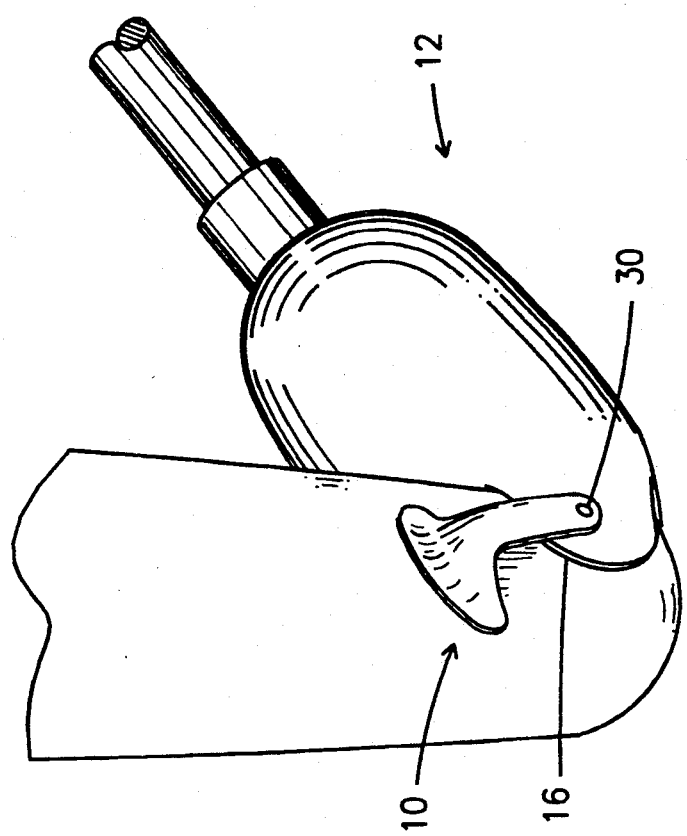
FIG. 7 is a perspective view of the parts shown in FIG. 6 when the knee of the wearer of the prosthesis is bent at an acute angle.

Referring now to the drawings, it will there be seen that the novel articulating supracondylar suspension device or base member is denoted as a whole by the reference numeral 10. A modified (upper rim cut off) PTB prosthesis equipped with the novel attachment device is denoted as a whole by the reference numeral 12.

Device or base member 10 is substantially rigid but is sufficiently flexible to conform to the contour of the residual limb in the manner shown hereinafter; a high impact plastic or other suitable material is the preferred material for making said base member. The flexibility of the device enables it to fit numerous individuals of differing bone structures, i.e., a prosthetist can purchase device 10 in quantity and it will fit virtually all patients. Thus, the need to custom fit a form-fitting upper rim for each patient is eliminated. As a practical matter, a smaller device 10 might be needed for pediatric patients, but such smaller device would fit virtually all smaller patients.

A conventional PTB/SC prosthesis is denoted 14 in FIG. 3. Novel prosthesis 12 has an uppermost rim 16 that is not formed to fit over the medial femoral condyle. In the claims that follow, said rim will accordingly be referred to as a flat rim, although it does of course circumscribe the residual limb. As those skilled in the art of prosthetics will recognize, the construction of such a socket is much simpler and less problematic than the construction of the PTB/SC having the form-fitting curvature 13 as shown in FIG. 3. By eliminating the step of fashioning such curvature, substantial reductions in casting, modification, and fabricating times, and the associated costs thereof, are realized. Moreover, less materials are needed because the novel PTB does not extend as high relative to the patient's knee, as can be gleaned from a comparison of FIGS. 3 and 4 which Figs. provide a side-by-side comparison of the prior art and novel prostheses, respectively. As mentioned earlier, novel PTB 12 can be made by simply cutting off the form-fitting rim of a prior art PTB, as is apparent from a comparison of said side-by-side FIGS.

Device 10 includes first end 20, second end 22, and neck 24 that is formed integrally with said first and second ends and which interconnects them. Mounting hole 26 is formed in second end 22 and is aligned with a mating mounting hole, not shown, formed in prosthesis 12 when the device is installed. Pivot pin 30 (FIGS. 6 and 7) defines the pivotal axis about which device 10 pivots when the patient bends his knee.

Note in FIGS. 1 and 2 that first end 20 includes a pair of laterally extending arms that extend in opposite directions relative to one another and in perpendicular relation to neck 24.

Figure 6:
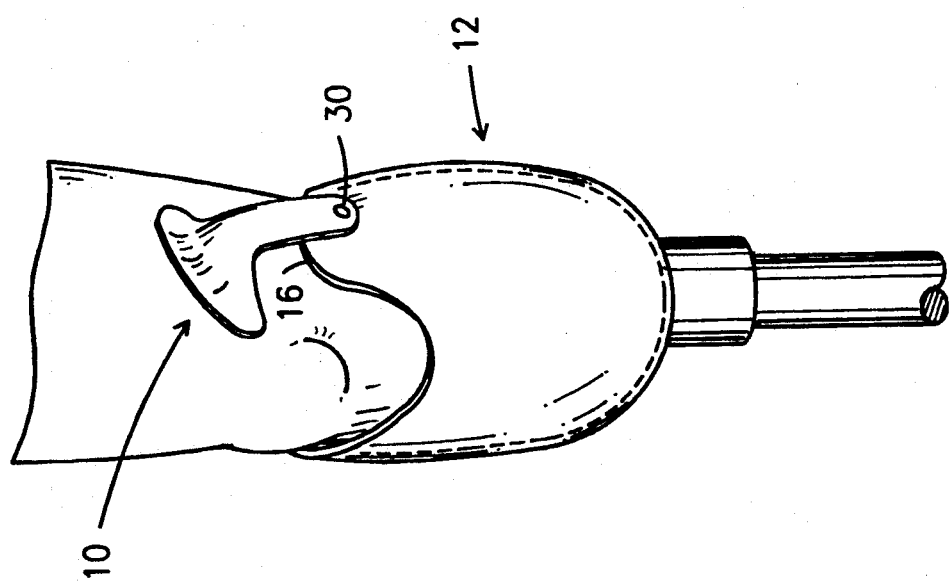
FIG. 6 is a perspective view showing a residual limb in a prosthesis provided with the novel device.

The inward curvature of neck 24 is perhaps best shown in FIGS. 4 and 5. This curvature causes convexity 32 to bear against the patient's knee above the medial femoral condyle as shown in FIGS. 4, 6, and 7; the radius of the curvature that produces the convexity is selected so that it is comfortable to the patient yet sharp enough to snugly and tightly fit over said bone. In a preferred embodiment, the radius of curvature indicated by arrow 40 (FIG. 5) is 3/16". The radius of curvature of the first part 20 in the anterior and posterior direction, indicated by arrow 39 in FIG. 2, is 3⅛", and the radius of curvature 41 (FIG. 5) of neck 24 is 1⅜". In the claims that follow, radius 39 forms a concavity that enables top part 20 of device 10 to at least partially circumscribe and to bear directly against the medial part of the residual limb (and which therefore centers device 10 with respect to the medial femoral condyle) is referred to as the first curvature, radius 40 that determines the amount of convexity of said top part is referred to as the second curvature, and the radius 41 of the neck 24 is referred to as the third curvature.

FIGS. 6 and 7 show how device 10 pivots with the socket while remaining in firm contact with the knee above the bone even when the knee is bent at an acute angle. It should be apparent from FIG. 7 that the molded curvature 13 (FIG. 3) of prior art socket 14 would be completely disengaged from the knee when said knee is bent as depicted in said FIG. 7.

A strap, not shown, may encircle the patient's leg and device 10 to further secure the device to said leg. The strap is adjustable in length so that each individual using device 10 may adjust the pressure with which convexity 32 (FIG. 4) bears against the leg above the bone. The tightness of the strap can also be adjusted throughout the day as required.

This invention is clearly new and useful. Moreover, it was not obvious to those of ordinary skill in this art at the time it was made, in view of the prior art considered as a whole as required by law.

It will thus be seen that the objects set forth above, and those made apparent from the foregoing description, are efficiently attained and since certain changes may be made in the above construction without departing from the scope of the invention, it is intended that all matters contained in the foregoing construction or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween.

Now that the invention has been described,
What is claimed is:

1. A prosthesis of the patella tendon bearing type, comprising:
   a prosthesis socket having a flat rim;
   an articulating supracondylar suspension means having a top part and a lower part;
   said lower part being pivotally mounted to said socket at a preselected location below said rim and said top part projecting upwardly above said rim;
   said top part adapted to bear against a residual limb when a residual limb is positioned in said socket;
   said top part adapted to bear against said limb above the medial femoral condyle of said limb;
   whereby said socket can be suspended from said limb.

2. The prosthesis of claim 1, wherein said top part has a first predetermined curvature formed therein, said first predetermined curvature enabling said top part to at least partially circumscribe the medial part of said residual limb.

3. The prosthesis of claim 2, wherein said top part has a second predetermined curvature formed therein, said second predetermined curvature defining a convexity that bears against the residual limb above said medial femoral condyle when said limb is positioned in said socket, said convexity extending the entire extent of said top part.

4. The prosthesis of claim 3, further comprising a neck means having a third predetermined curvature, said neck means interconnecting said top part and said bottom part of said suspension means.

5. A device that maintains a prosthesis socket on a residual limb, comprising:
   a substantially rigid but flexible base member;
   said base member having a top part, a lower part, and a neck means that interconnects said top and lower parts;
   said top part having a first predetermined curvature forming a concavity that enables said top part to at least partially circumscribe a residual limb with the concavity adapted to bear directly against said limb.
   said top part having a second predetermined curvature forming a convexity that extends the extent of said top part and which is adapted to bear against said residual limb above a preselected bone in said limb;
   an aperture formed in said lower part;
   said aperture defining a pivot point about which said base member may pivot;
   said top part being adapted to bear directly against said residual limb when said residual limb is not bent and said top part being adapted to bear directly against said residual limb when said residual limb is bent, said base member pivoting about said pivot point when said residual limb is bent;
   said neck means having a predetermined curvature so that said top part can bear against said residual limb above said preselected bone to thereby suspend said prosthesis from said preselected bone;
   whereby the pivotal mounting of said base member to said socket maintains the socket on the residual limb even when the knee of said residual limb is bent at an acute angle.

6. The device of claim 5, wherein said top part includes a pair of arms, integral to said neck means, that extend in opposite directions relative to one another in substantially perpendicular relation to said neck means.

* * * * *